United States Patent
Eppstein et al.

(10) Patent No.: US 6,685,699 B1
(45) Date of Patent: Feb. 3, 2004

(54) SELF-REMOVING ENERGY ABSORBING STRUCTURE FOR THERMAL TISSUE ABLATION

(75) Inventors: Jonathan A. Eppstein, Atlanta, GA (US); Stuart McRae, Atlanta, GA (US)

(73) Assignees: SpectRx, Inc., Norcross, GA (US); Altea Therapeutics Corp., Tucker, GA (US)

(*) Notice: Subject to any disclaimer, the term of this patent is extended or adjusted under 35 U.S.C. 154(b) by 50 days.

(21) Appl. No.: 10/018,015

(22) PCT Filed: Jun. 7, 2000

(86) PCT No.: PCT/US00/15665
§ 371 (c)(1),
(2), (4) Date: Apr. 1, 2002

(87) PCT Pub. No.: WO00/74583
PCT Pub. Date: Dec. 14, 2000

Related U.S. Application Data

(60) Provisional application No. 60/138,193, filed on Jun. 9, 1999.

(51) Int. Cl.[7] .............................................. A61B 18/18
(52) U.S. Cl. ............................. 606/2; 606/9; 606/606; 606/13
(58) Field of Search ............................. 606/2, 3, 9, 13; 604/20, 22

(56) References Cited

U.S. PATENT DOCUMENTS

| | | | |
|---|---|---|---|
| 4,775,361 A | 10/1988 | Jacques et al. | |
| 5,092,864 A | * 3/1992 | Hayes et al. | 606/10 |
| 5,643,252 A | 7/1997 | Waner et al. | |
| 5,885,211 A | 3/1999 | Eppstein et al. | |
| 6,173,202 B1 | * 1/2001 | Eppstein | 604/20 |
| 6,334,851 B1 | * 1/2002 | Hayes et al. | 600/573 |

FOREIGN PATENT DOCUMENTS

| | | |
|---|---|---|
| EP | A 256806 | 8/1987 |
| EP | 0256806 | 2/1988 |
| WO | WO 98/42267 | 10/1998 |
| WO | WO 99/40848 | 8/1999 |
| WO | WO 99/44638 | 9/1999 |
| WO | WO 00/04832 | 2/2000 |

* cited by examiner

Primary Examiner—Roy D. Gibson
(74) Attorney, Agent, or Firm—Needle & Rosenberg, P.C.

(57) ABSTRACT

A device to facilitate ablation of tissue, such as for forming one or more openings in the tissue for transdermal monitoring and/or delivery applications. The device comprises: (a) a support layer having at least one aperture therein, and (b) at least one energy absorbent film layer disposed over the at least one aperture in the support layer for making substantial contact with tissue through the aperture. The at least one energy absorbent film layer is under a tension force and absorbs energy focused thereon to thermally ablate the tissue. After ablation, the layer breaks apart allowing access to the ablated tissue beneath it.

18 Claims, 6 Drawing Sheets

SELF-REMOVING ENERGY ABSORBING STRUCTURE FOR THERMAL TISSUE ABLATION

CROSS REFERENCE TO RELATED APPLICATION

The present application is a 35 U.S.C. §371 national phase application from, and claims priority to, international application PCT/US00/15665, filed Jun. 7, 2000 (published under PCT Article 21(2) in English), which claims priority to U.S. Provisional Application Ser. No. 60/138,193, filed Jun. 9, 1999, which application is hereby incorporated herein in their entirety.

FIELD OF THE INVENTION

This invention relates to the field of tissue ablation for the formation of openings in the tissue. In particular, this invention relates to self-removing energy absorbing structures for achieving thermal tissue ablation.

BACKGROUND OF THE INVENTION

The flux of a drug or analyte across a biological tissue can be increased by changing the diffusion coefficient or the gradient for diffusion. Commonly, the flux is enhanced by increasing the permeability of the skin, such as by chemical penetration enhancers, iontophoresis, and poration techniques.

Thermal tissue ablation for forming openings in tissue is disclosed in commonly assigned U.S. Pat. No. 5,885,211 to Eppstein, et al. There is room for improving the thermal tissue ablation process.

SUMMARY OF THE INVENTION

The present invention is directed to a device to facilitate ablation of tissue, such as for forming one or more openings in the tissue for transdermal monitoring and/or delivery applications. The device comprises: (a) a support layer having at least one aperture therein, and (b) at least one energy absorbent film layer disposed over at least one aperture in the support layer for making substantial contact with tissue through the aperture. The at least one energy absorbent film layer is under a tension force over or across the aperture and absorbs energy focused thereon to thermally ablate the tissue. After ablation, and because it is under tension, the film layer breaks apart allowing access to the ablated tissue beneath it.

The present invention is further directed at a method for forming openings in a tissue comprising the steps of: (a) positioning a support layer having an aperture therein on a tissue; (b) positioning an energy absorbent film layer over the aperture to make substantial contact with the tissue through the aperture; and (c) focusing energy onto the energy absorbent film layer to conduct heat to the tissue thereby ablating the tissue.

The above and other advantages of the present invention will become more readily apparent when reference is made to the following description taken in conjunction with the accompanying drawings.

DETAILED DESCRIPTION OF THE INVENTION

The present invention may be understood more readily by reference to the following detailed description of various embodiments of the invention and the Figures.

Before the present articles and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Ranges may be expressed herein as from "about" or "approximately" one particular value and/or to "about" or "approximately" another particular value. When such a range is expressed, another embodiment comprises from the one particular value and/or to the other particular value. Similarly, when values are expressed as approximations, by use of the antecedent "about," it will be understood that the particular value forms another embodiment.

As used herein, "opening" means any size hole, aperture or pore of any depth, that is capable of substance transport therethrough. Inclusive in this term is at least one opening in the tissue sized no larger than about 1000 μm in diameter called a micropore.

Throughout this application, where publications are referenced, the disclosures of these publications in their entireties are hereby incorporated by reference into this application in order to more fully describe the state of the art to which this invention pertains.

Figure 1:
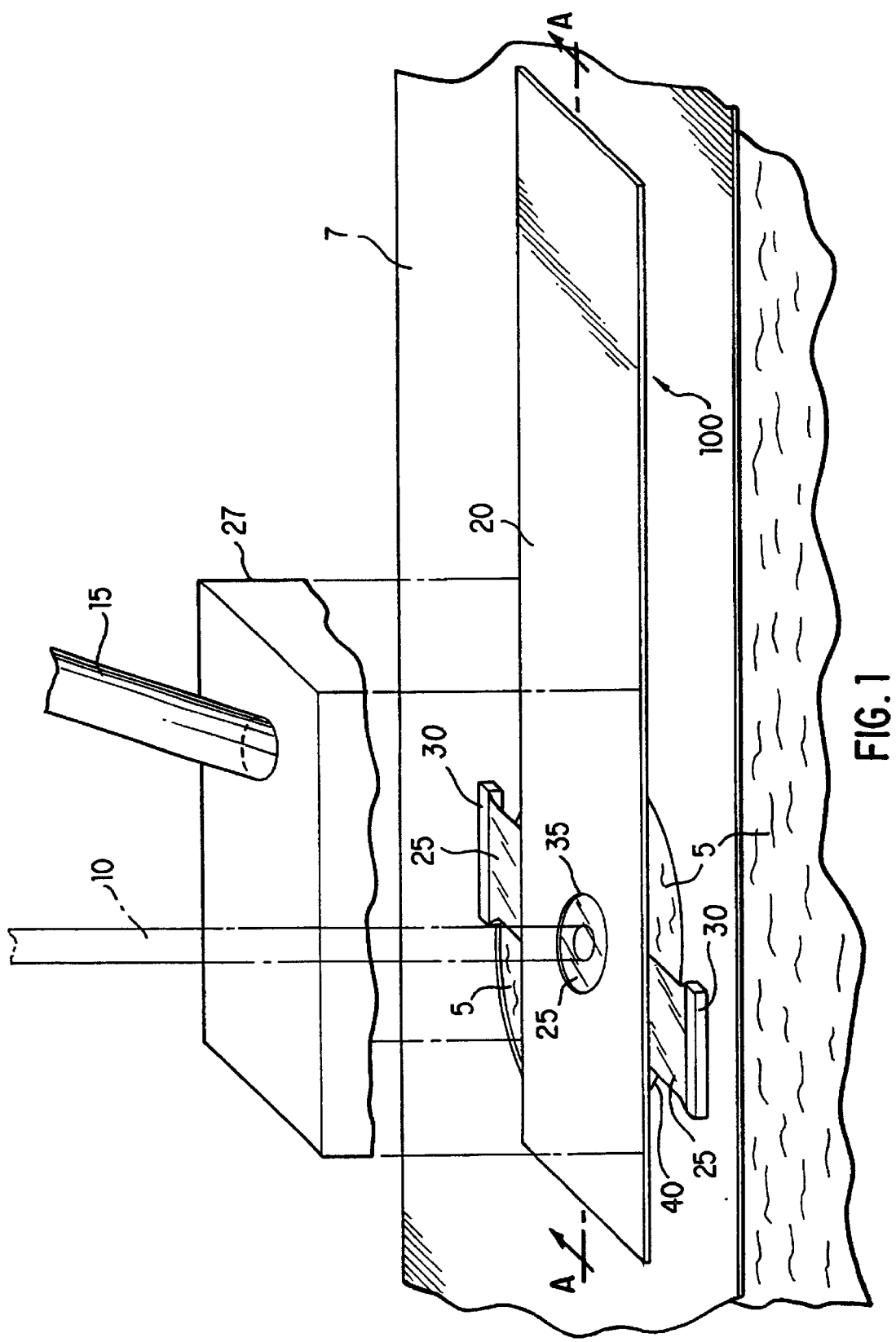
FIG. 1 is a perspective view of one embodiment of a portion of the device of the present invention.
Figure 2:
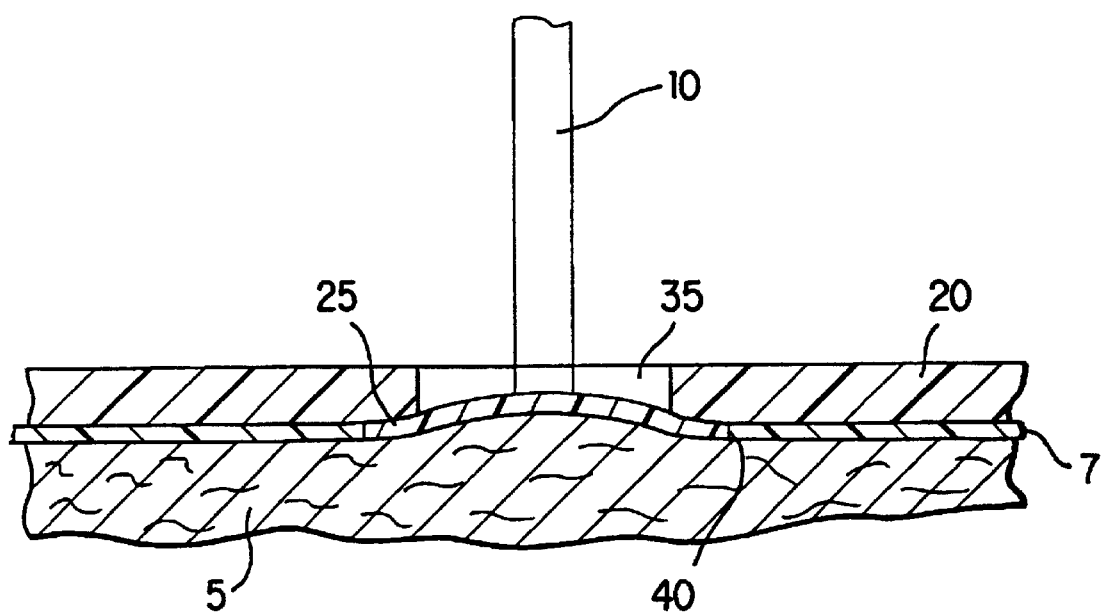
FIG. 2 is cross-sectional view taken through line A—A of FIG. 1 and illustrating the relationship of the energy absorbent film to the tissue when suction is applied to the device.
Figure 3:
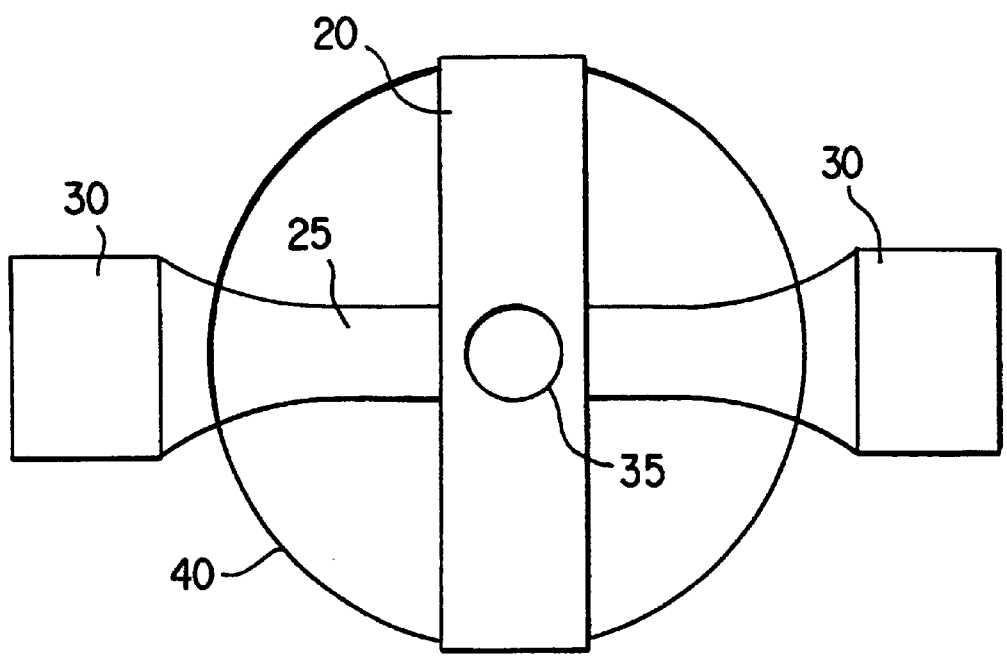
FIG. 3 is a top view of one embodiment of a portion of the device showing the energy absorbent film before it has been affected by energy.

Referring first to FIGS. 1–3, one embodiment of a portion of the present invention 100 is shown. The device 100 includes at least a support layer 7 and an energy absorbent film layer 25. Depending on the application of the device 100, it also includes an optional assay reagent pad 20. The energy absorbent film layer 25 is stretched or otherwise placed under tension across a hole or aperture 40 in the support layer 7. At least one hole or aperture 35 is provided in the assay reagent pad 20 above the hole 40 and the energy absorbent film 25. The hole(s) 35 may be any shape or size to provide a suitable site for tissue ablation.

In one embodiment of the invention, the energy absorbent film layer 25 of FIG. 1 is held in place and under tension across the aperture 40 by at least one tension member 30. This tension member(s) 30 may be constructed of any suitable material in any shape to create a tension force across the film 25. In one form, at least one tension member 30 is provided at one end of the energy absorbent film layer 25 and the other end is fixed to the support layer 7 by other suitable means, such as by glue or spot weld attachment. In another form, at least one tension member 30 is provided at both ends of the energy absorbent film layer 25 to hold it under tension across the aperture 40. Examples of materials suitable for the tension member(s) 30 include elastic, rubber, metal springs, or plastic springs or the like.

In another embodiment of the invention, tension members 30 are not needed and the film 25 is anchored directly to the support layer 7. Such anchoring may be performed by any suitable means including adhesive bonding, electromagnetic bonding, hot plate welding, induction bonding, insert bonding, radio-frequency sealing, spot welding, thermostacking, chemical bonding, thermo bonding, vibration welding or ultrasonic welding. Examples of film 25 suitable for such use without tension members include pre-stretched mylar, rubber, silicone, polycarbonate, polyurethane, polyvinyl chloride, or polypropylene film.

The support layer 7 serves to support the film 25 across the aperture 40. As such, suitable materials for the support layer 7 include polyester, ceramic, polycarbonate (PC), polyvinylchloride (PVC), and mixtures thereof. This support layer can be of any suitable thickness to maintain structural support for the film 25.

The optional assay reagent pad 20 serves to detect the presence of a substance in the fluid. For example, the assay reagent pad 20 may be useful in detecting the presence of an analyte (such as glucose) in blood or interstitial fluid. The assay reagent pad 20 may be constructed of any suitable material, with as many layers or materials as necessary for detecting the presence of a substance in a fluid. Elements of the assay reagent pad include electrodes, one or more enzymes, and one or more indicators as is well known in the electrochemical biosensor art. The assay reagent pad 20 alternatively may be a type that is optically interrogated to determine a measurement of an analyte. The assay reagent pad 20 may be attached to the film 25 or may be placed proximate to the film 25 such that the pad 20 is capable of fluid communication with the film 25.

The energy absorbent film layer 25 includes a layer of material that absorbs energy and heats up. As the energy absorbent film layer 25 is heated by a beam or field 10 of energy, the film 25 transfers heat to the tissue by conduction, thereby ablating the tissue. One use of ablating the tissue is to form one or more openings in the tissue for transdermal monitoring or delivery applications. Thermal tissue ablation for forming openings is described more fully in U.S. Pat. No. 5,885,211.

Any suitable energy may be used for the beam of energy 10 to heat the energy absorbent film 25. In one embodiment, the beam of energy 10 is a beam of optical energy, which may for example be provided by a laser diode. In another embodiment, the energy 10 is comprised of electromagnetic energy, laser, gamma radiation, and/or beta radiation, etc.

The types of energy absorbing substances that are suitable for the film 25 include those disclosed in commonly assigned U.S. Pat. No. 5,885,211, and in commonly assigned PCT/0599/04929, filed Mar. 5, 1999, both of which are incorporated herein by reference in their entireties. Copper pythalocyanine doped film is an example of a suitable film 25 material. Alternatively, a clear film 25 with an absorbent adhesive layer can be used whereby the adhesive provides a positive attachment to the targeted tissue, and a thermal conduction path to the tissue. Once the aperture 40 is formed and the film 25 is retracted from the opening, the adhesive also serves to help stretch the aperture 40 and the attached tissues beneath the surface, increasing the flux rate to facilitate extraction or delivery of substances via the aperture 40.

The operation of the device will now be described with reference to FIGS. 1–4. As shown in FIG. 1, a vacuum or suction 15 is applied (by a vacuum source not shown) to a region 27 of the device 100 so as to pull the tissue 5 up to contact the film 25 through the aperture 40 of the support layer 7 (FIG. 2). The film 25 flexes to provide good physical contact with the underlying tissue 5 which is desirable to achieve efficient transfer of heat to the tissue when the energy absorbent film layer 25 is heated.

Figure 4:
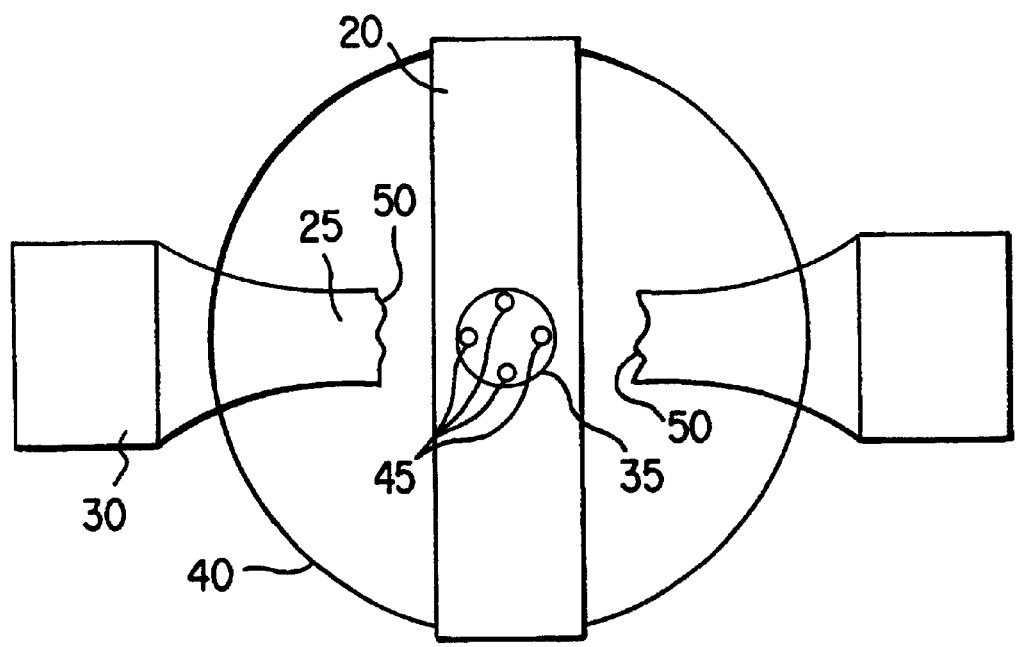
FIG. 4 is a top view of one embodiment of a portion of the device showing the energy absorbing layer after it has been affected by energy.

The beam or field 10 of energy is then directed onto the energy absorbent film 25. In response, the film 25 heats up and the heat in the film is transferred by conduction to the tissue 5, thereby ablating the tissue. As the film 25 absorbs the energy and transfers it to the tissue, eventually, because of the tension force, it breaks and separates across the aperture 40 as illustrated in FIG. 4. The film 25 burns up as the thermal ablation process occurs and in so doing is weakened to be overcome by the tension force. This self-removal or self-separating feature of the film 25 allows access to the ablated area of the tissue to facilitate fluid communication with the opening(s) 45 without any additional steps.

Figure 5:
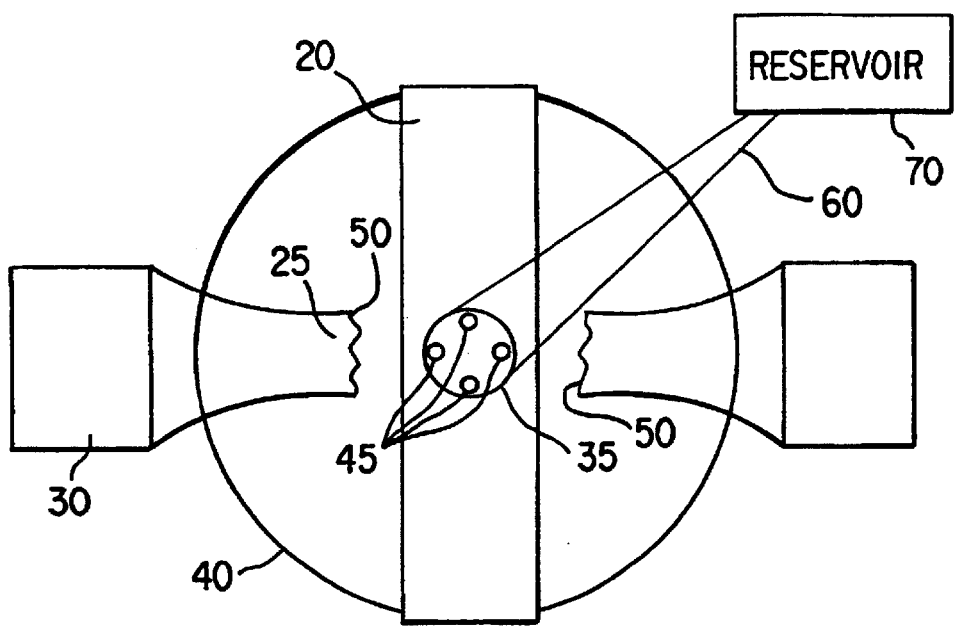
FIG. 5 is a top view of one embodiment of a portion of the device used as part of a transdermal delivery system.

FIG. 5 depicts the device 100 used in connection with a transdermal delivery system wherein at least one drug or agent is delivered to the tissue 5 via the opening(s) in the tissue 45. A reservoir 70 containing the at least one drug or agent may be in fluid communication with the opening(s) in the tissue 45 via a conduit 60, such as tubing. Alternatively, the reservoir 70 may be integrally formed with the support layer 7 so that the at least one drug or agent can be delivered into the tissue 5 in a single step procedure with gravity or pressure forcing the drugs or agents into the tissue 5.

Figure 6:
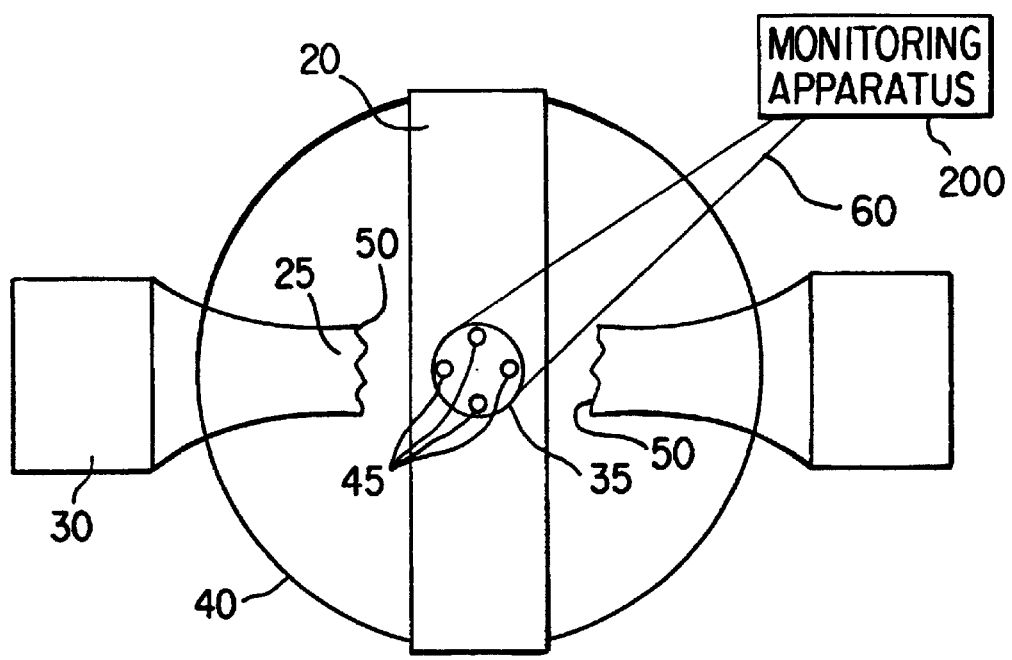
FIG. 6 is a top view of one embodiment of a portion of the device used as part of a monitoring system.

FIG. 6 shows the device 100 used in connection with a monitoring system. The assay reagent pad 20 may be located on the device 100 and connected (wired or wirelessly) to a monitoring apparatus 200. Alternatively, the assay reagent pad 20 may be located remotely in the monitoring apparatus 200 and coupled via fluid conduit 60 that carries the fluid.

Whether the assay reagent pad 20 is located remote or proximate to the opening(s) in the tissue 45 depends on the specific application. Both embodiments are useful in discrete monitoring applications for analyzing fluid on a single use basis, as well as in continuous monitoring applications for continuously extracting and analyzing fluid over a longer term basis, such as several hours, days, etc. See, for example, International Application No. PCT/US99/16378, filed Jul. 20, 1999, entitled "System and Method for Continuous Analyte Monitoring".

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A device to facilitate thermal ablation of tissue, comprising:
   (a) a support layer having at least one aperture therein; and
   (b) at least one energy absorbent film layer disposed over the at least one aperture in the support layer for making substantial contact with tissue through the aperture, wherein the at least one energy absorbent film layer is under a tension force; and absorbs energy focused thereon to thermally ablate the tissue.

2. The device of claim 1, further comprising an assay pad disposed proximate the aperture in the support layer.

3. The device of claim 2, wherein the assay pad has at least one aperture aligned with the at least one aperture in the support layer.

4. The device of claim 1, wherein the energy absorbent film layer heats up by absorbing energy focused thereon and conducts heat to the tissue thereby ablating the tissue and causing it to break apart over the aperture.

5. The device of claim 1, and further comprising at least one tension member that holds the at least one energy absorbent film layer under tension over the aperture.

6. The device of claim 5, wherein the at least one tension member is comprised of a member selected from the group consisting of elastic, rubber, metal springs, or plastic springs.

7. The device of claim 1, further comprising a reservoir containing at least one drug or agent for release into the tissue.

8. The device of claim 1, wherein the support layer is comprised of: polyester, ceramic, polycarbonate (PC), polyvinylchloride (PVC), or mixtures thereof.

9. The device of claim 1, wherein the at least one energy absorbent film layer is comprised of copper pythalocyanine.

10. The device of claim 1, wherein the at least one energy absorbent film layer is anchored at ends thereof directly to the support layer.

11. The device of claim 1, wherein the at least one energy absorbent film layer is flexible so as to make contact with the tissue through the aperture when vacuum is applied over the aperture of the support layer.

12. The device of claim 1, wherein the energy absorbent film layer is responsive to energy from the group consisting of; electromagnetic energy, optical energy, gamma radiation, and/or beta radiation.

13. A method for forming openings in a tissue comprising the steps of:
   (a) positioning a support layer having an aperture therein on a tissue;
   (b) positioning an energy absorbent film layer over the aperture to make substantial contact with the tissue through the aperture; and
   (c) focusing energy onto the at least one energy absorbent film layer to conduct heat to the tissue thereby ablating the tissue.

14. The method of claim 13, further comprising the step of applying vacuum over the aperture to draw the tissue into substantial physical contact with the energy absorbent film layer.

15. The method of claim 13, wherein the energy absorbent film layer breaks apart to provide access to the tissue via the aperture.

16. The method of claim 13, further comprising the step of positioning an assay pad in fluid communication with the tissue via the aperture.

17. The method of claim 13, further comprising the step of contacting the tissue with at least one drug or agent.

18. The method of claim 13, wherein the step of focusing energy comprises focusing energy selected from the group consisting of electromagnetic energy, optical energy, gamma radiation, or beta radiation.

* * * * *